United States Patent
Ludwig et al.

(10) Patent No.: US 9,398,450 B2
(45) Date of Patent: Jul. 19, 2016

(54) MOBILE SURVEY TOOLS WITH ADDED SECURITY

(71) Applicant: SURVEYMONKEY INC., Palo Alto, CA (US)

(72) Inventors: Phillip John Ludwig, San Francisco, CA (US); Stuart Loh, Menlo Park, CA (US); David Whitfield Morriss, Nashville, TN (US); Sean Duncan Holbert, San Francisco, CA (US)

(73) Assignee: SURVEYMONKEY, INC., Palo Alto, CA (US)

( * ) Notice: Subject to any disclaimer, the term of this patent is extended or adjusted under 35 U.S.C. 154(b) by 78 days.

(21) Appl. No.: 14/170,314

(22) Filed: Jan. 31, 2014

(65) Prior Publication Data

US 2015/0223056 A1   Aug. 6, 2015

(51) Int. Cl.
| | |
|---|---|
| *H04M 1/66* | (2006.01) |
| *H04W 12/02* | (2009.01) |
| *H04L 29/06* | (2006.01) |
| *H04W 12/08* | (2009.01) |
| *H04W 12/06* | (2009.01) |
| *G06F 19/00* | (2011.01) |
| *G06F 21/62* | (2013.01) |
| *H04W 88/02* | (2009.01) |

(52) U.S. Cl.
CPC .............. *H04W 12/02* (2013.01); *G06F 19/32* (2013.01); *G06F 21/6245* (2013.01); *H04L 63/083* (2013.01); *H04W 12/06* (2013.01); *H04W 12/08* (2013.01); *H04W 88/02* (2013.01)

(58) Field of Classification Search
CPC ... H04L 63/083; G06F 21/31; G06F 21/6245; G06F 21/60; G06F 2221/2117; G06F 2221/2119; G06F 2221/2129; G06F 21/62; G06Q 20/3674; G06Q 30/06; G06Q 40/02; G06Q 20/382; G06Q 20/08; G06Q 20/383; G06Q 20/40
USPC ......... 455/411, 410, 418; 726/4, 1, 5, 9, 7, 6, 726/28, 11, 20; 705/26.1, 318, 64, 72, 75; 713/183

See application file for complete search history.

(56) References Cited

U.S. PATENT DOCUMENTS

| | | | |
|---|---|---|---|
| 2006/0116918 A1* | 6/2006 | Flora | G06Q 10/063116 705/7.19 |
| 2007/0113294 A1* | 5/2007 | Field | H04L 63/083 726/27 |
| 2009/0025080 A1* | 1/2009 | Lund | H04L 9/3273 726/15 |
| 2009/0276847 A1* | 11/2009 | Kotaka | 726/17 |
| 2012/0233674 A1* | 9/2012 | Gladstone | H04L 9/085 726/6 |
| 2013/0096985 A1* | 4/2013 | Robinson et al. | 705/7.32 |
| 2014/0122716 A1* | 5/2014 | Santhiveeran | H04L 63/0272 709/225 |
| 2014/0129435 A1* | 5/2014 | Pardo et al. | 705/41 |
| 2014/0344904 A1* | 11/2014 | Venkataramani et al. | 726/5 |

* cited by examiner

*Primary Examiner* — Fred Casca
(74) *Attorney, Agent, or Firm* — Marger Johnson

(57) ABSTRACT

A system includes a server computing device executing code to provide a privacy-enabled service to users, and a mobile computing device able to access the server. The mobile device further able to open a user interface on the mobile device, receive a user name and password through the user interface, determine that the application is privacy-enabled, notify the user that the application is privacy-enabled and prompting the user for an application passcode, and receive the passcode from the user.

10 Claims, 5 Drawing Sheets

FIGURE 5
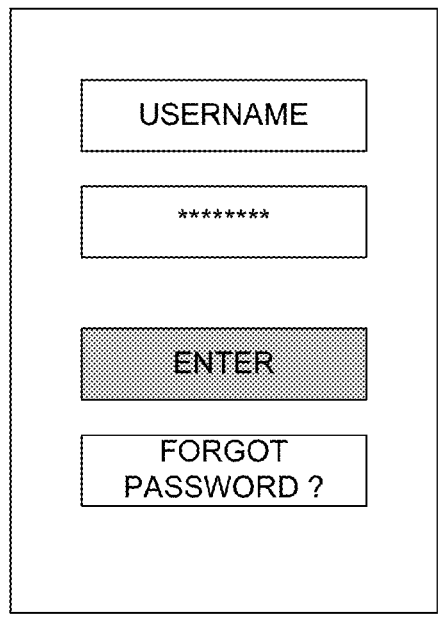
FIGURE 6
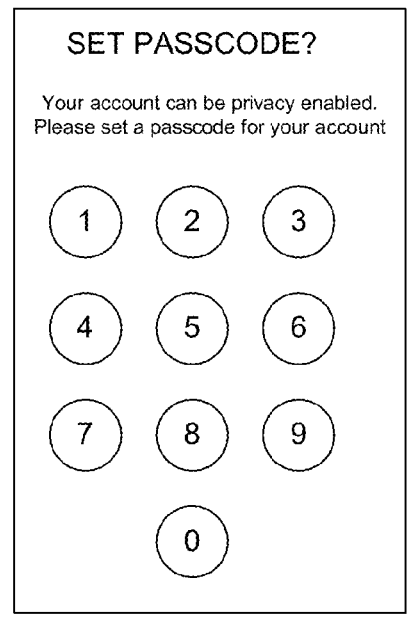
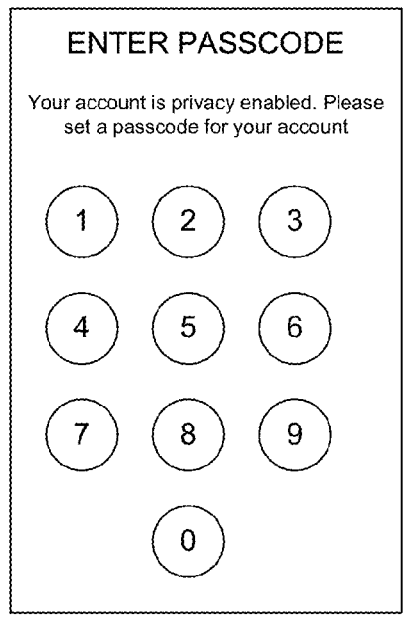
FIGURE 7

MOBILE SURVEY TOOLS WITH ADDED SECURITY

BACKGROUND

Many enterprises have begun to employ surveys as tools to track their customer service, product reviews, etc. Some of these enterprises provide services related to sensitive information, such as health care information that falls under HIPAA (Health Insurance Portability and Accountability Act), financial information, identity-related information, etc.

With the advent of smart phones, tablets, and other similar devices, survey providers may create applications that provide a direct portal to their survey tools over the Internet. Users employing the application may inadvertently leave them 'open' on their mobile devices. This may cause concern because of the sensitive nature of the information that may be accessible on the mobile devices.

Many of these applications provide security through the portal to the service itself, through user name and password access that the user enters when the application connects to the service. Many of these user name and password processes may include a 'site key' such as a picture or graphic that verifies to the user that the user is on a legitimate site. However, there is very little security provided at the device level.

BRIEF DESCRIPTION OF THE DRAWINGS

FIG. 5 shows an example of a user interface to allow access to a provider web site.

FIG. 6 shows an embodiment of a user interface for enabling privacy in an application.

FIG. 7 shows an embodiment of a user interface for a previously enabled privacy application.

DETAILED DESCRIPTION OF THE EMBODIMENTS

Figure 1:
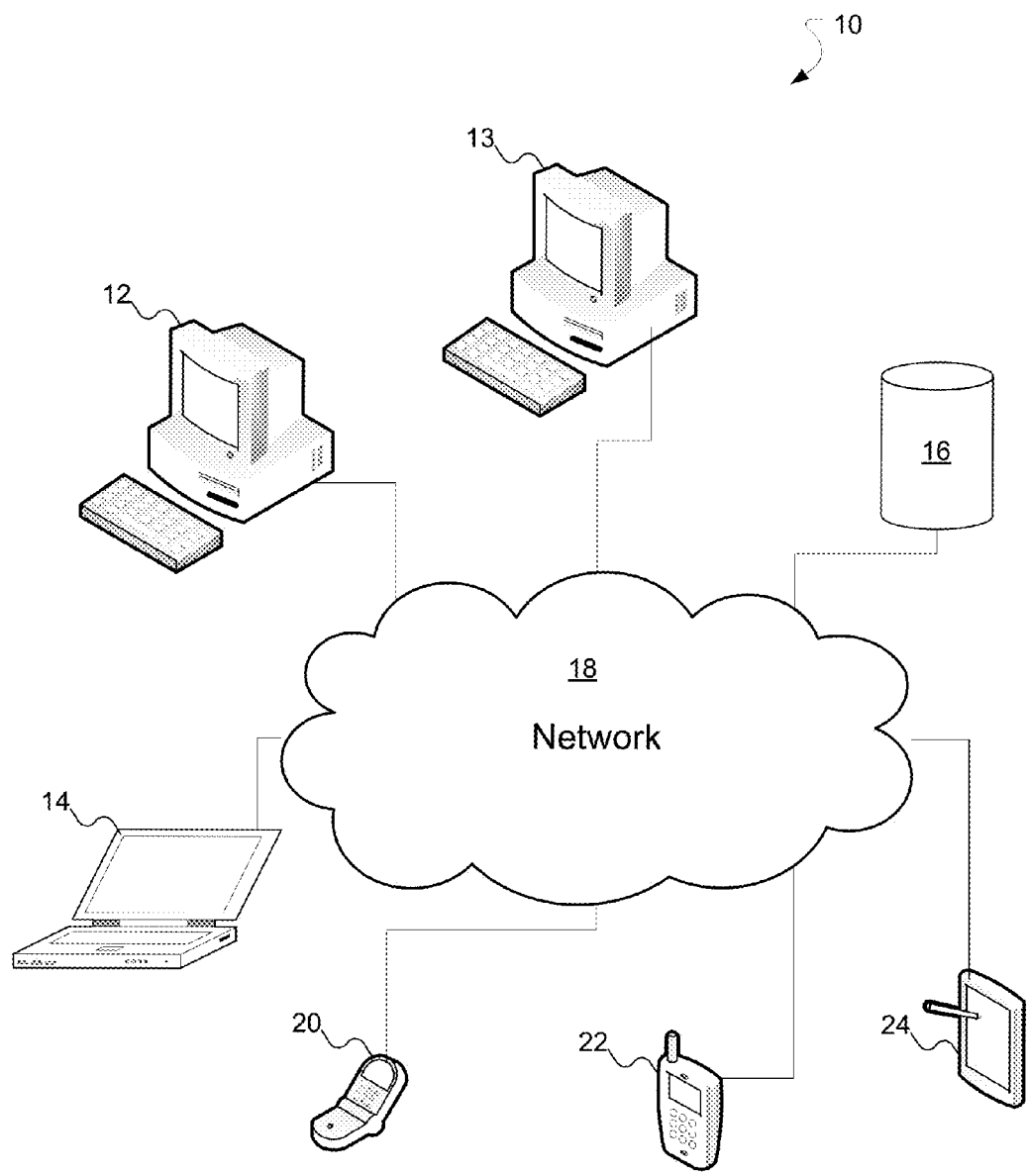
FIG. 1 shows an embodiment of a system having a mobile device, a network and a server.

FIG. 1 shows an example of a networked system 10 in accordance with certain embodiments of the disclosed technology. In this example, the system 10 includes a network 18 such as the Internet, an intranet, a home network, a public network, or any other network suitable for implementing the embodiments discussed here. In the example, a provider server 12 or other computing device may connect to the network 18 to communicate with each other or with other devices connected to the network. Similarly, a provider server may comprise multiple computing devices such as 12 and 13 that connect to the network 18. One should note that the term 'service' is used in the simplest form of the term, that of supplying a capability or activity to a user, rather than in any particular definition in networks, such as an application running in the network application layer. The discussion below may address a particular service provider, that of providing survey tools and surveys, to customers, but no limitation to such a service is intended, nor should any be implied.

The system 10 may also include three mobile electronic devices 20, 22 and 24 as examples of a user's computing device. Two of the mobile electronic devices 20 and 22 may be communications devices such as may be cellular telephones or smartphones. Another of the mobile devices 24 may be a handheld computing device such as a personal digital assistant (PDA), tablet device, or other portable device. A storage device 16 may store some of all of the data that is accessed or otherwise used by any or all of the computers 12 and 14 and mobile electronic devices 20, 22 and 24. The storage device 16 may be local or remote with regard to any or all of the computers 12, 14 and mobile electronic devices 20-24. The storage device may consist of one or more databases, as will be discussed in more detail later, and may actually consist of one or many physical memory devices. One must note that the system of FIG. 1 is merely intended as an example to demonstrate possible devices connected to a network.

Figure 2:
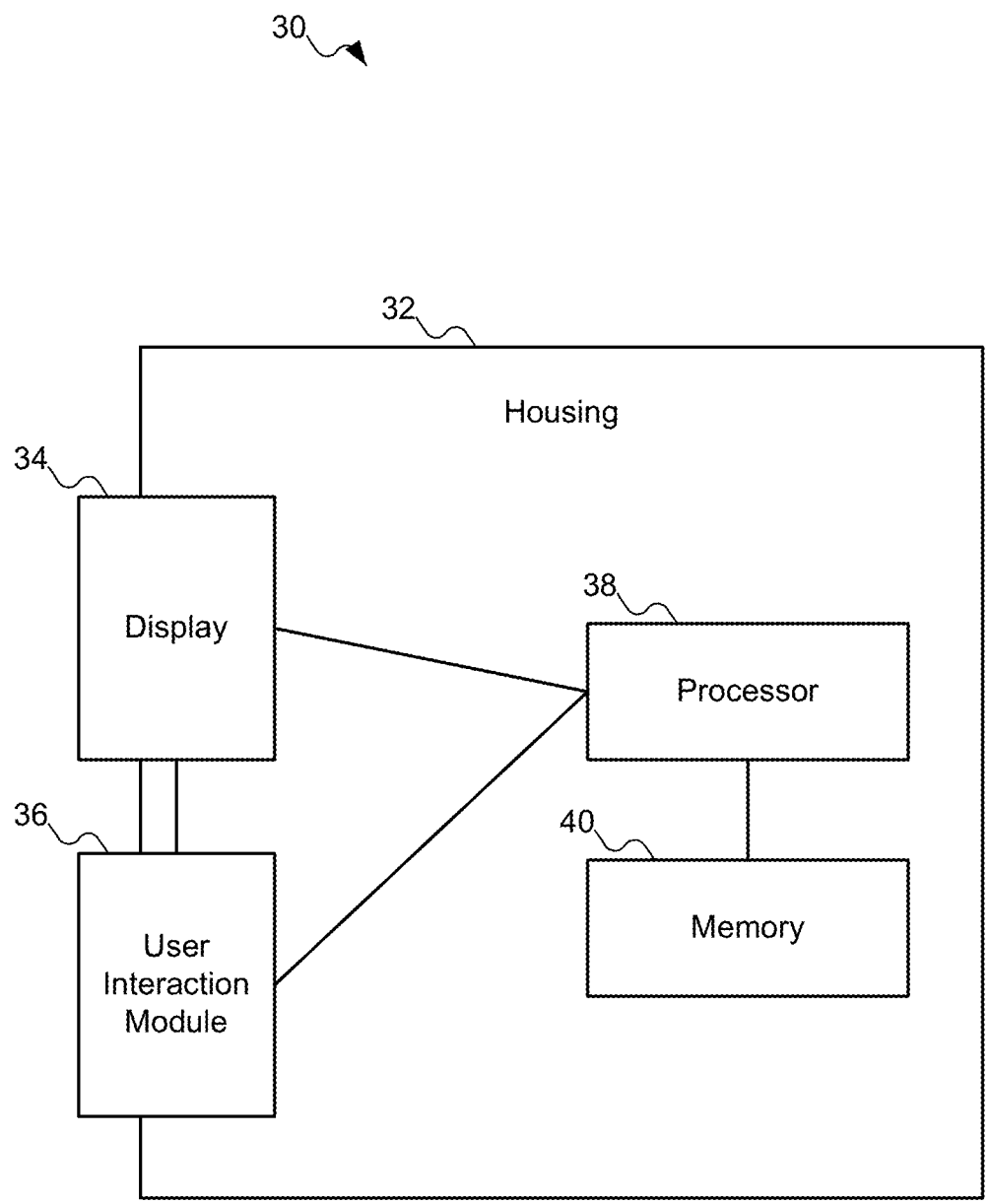
FIG. 2 shows a block diagram of an embodiment of a mobile computing device.

FIG. 2 illustrates an example of a mobile electronic device 30, such as any of the devices of FIG. 1, in which certain aspects of various embodiments of the embodiments may be implemented. The mobile device 30 may include, a PDA or tablet computing device, a mobile communications device such as a smartphone, an industry-specific machine such as a self-service kiosk or automated teller machine (ATM), or any other electronic device suitable for use in connection with certain embodiments of the disclosed technology. The term 'mobile' as used here means that the device can connect to the network without wires or cables, although the device may connect to the network using cables and wires in addition to its wireless capability.

In the example, the electronic device 30 includes a housing 32, a display 34 in association with the housing 32, a user interaction module 36 in association with the housing 32, a processor 38, and a memory 40. The user interaction module 36 may include a physical control device, such as a keyboard, mouse, microphone, speaking, or any combination thereof, or a virtual device, such as a virtual keypad implemented within a touchscreen. The processor 38 may perform any of a number of various operations. The memory 40 may store information used by or resulting from processing performed by the processor 38. The display will allow the user to see a user interface generated by an application on the mobile device with the appropriate input fields, etc.

An 'application' as that term is used here means a set of software instructions or codes that are executed on the mobile device that connect the mobile device to the service provider's server. The application generally has an icon that appears on the mobile device's screen. The user selects that application, such as by a touch to the touch screen, to start or launch the application. The application then provides the user with access to the service provider's services. As mentioned above, the application here provides a link or portal to a survey provider's website, as an example.

Typically, the service provider allows the user to access the website by entry of the user's user name and password. If the user had previously logged in by entering these through the application, the user may remain logged in until the user actively logs out, or some period of inactivity passes and the provider logs the user out. The website may also have added security features such as site keys, in which the user is presented with an image or other piece of information that is unique to the user, or security questions that identify the user to the website.

Some applications allow access to sensitive information such as health-related information about the user such as information protected by HIPAA, banking information, identity-related information, etc. The website level access is often considered sufficient by most providers, but there are opportunities to provide further security related to the application on the user's mobile device.

Many users are familiar with the ability to lock their mobile devices with a passcode. The user selects the ability to use a passcode in the mobile device's settings menu, and the passcode is used to secure the 'entire' device. This means that once the device is locked, either directly by the user, or by some period of inactivity passing, the user must enter the passcode to access any aspect of the mobile device. This type of passcode will be referred to as a device passcode.

The embodiments here address an application-level passcode that is similar to a device passcode, but are specific to the application itself. When the user activates the application, the application may require the user to enter another passcode to access the application. One should note that the passcode is on the device itself, separate from the user name and password used to access the website. Alternatively, the user may activate the application and the application only requires the passcode if the user has been inactive on the application for some predetermined period of time, or if the user has not logged into the website recently, etc. The application that has an application passcode will be referred to as a privacy-enabled application.

Figure 3:
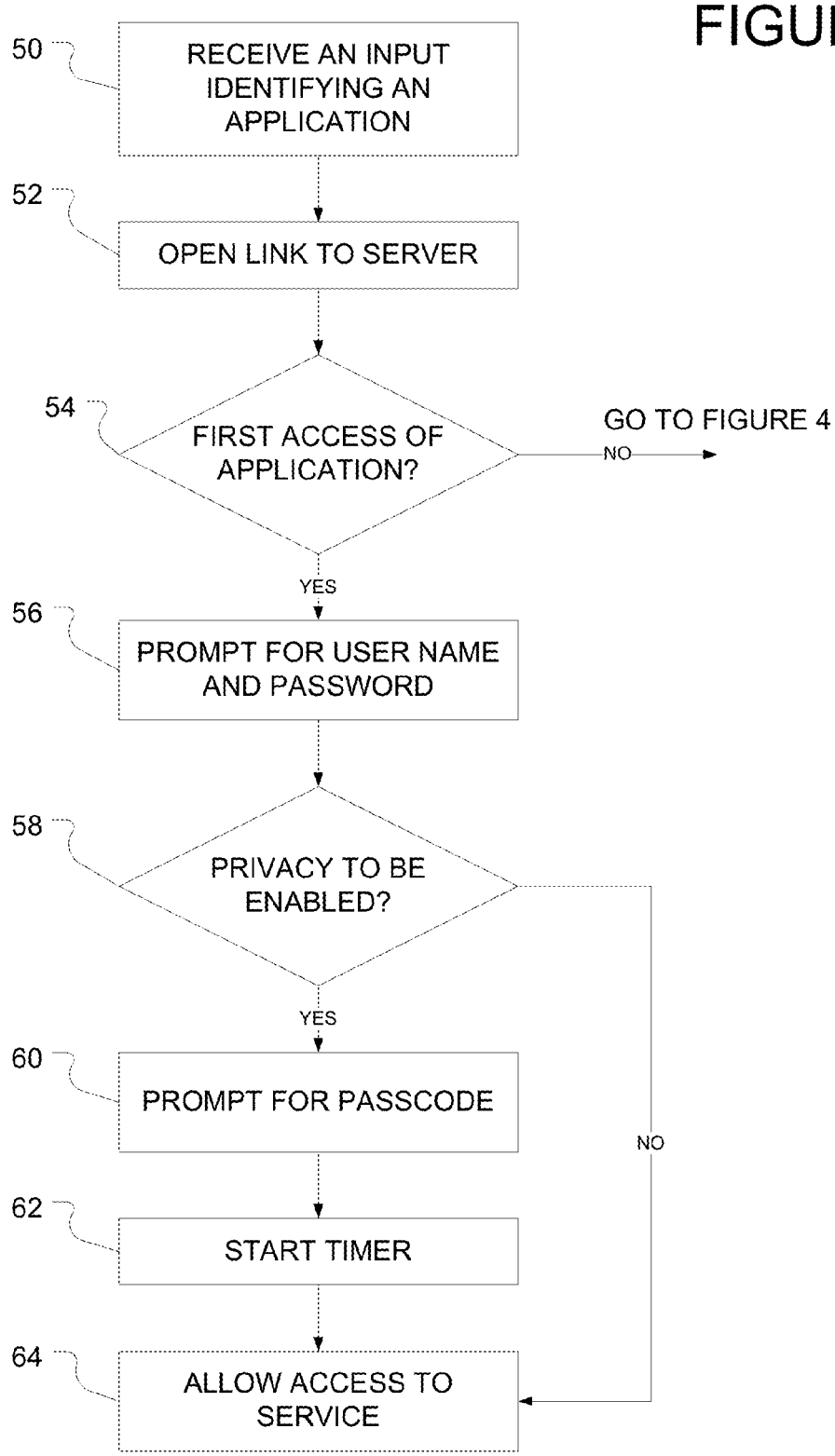
FIG. 3 shows an embodiment of a method of enabling privacy for an application on a mobile device.

FIG. 3 shows a flowchart of an embodiment of a method of providing a privacy-enabled application. The user identifies an application the user wants to access at 50. Typically, the user touches an icon or other representation of the application on the user interface of the user's mobile device. The application then launches and opens a link to the server at 52. One should note that the order of opening the link to the website and the passcode entry, etc., may occur differently than shown here. If this is the first access of the application by the user at 54, the application prompts for the user name and password 56 in a user interface similar to that shown in FIG. 5. Again, the order of asking for the user name and password, opening the link, etc. is left up to the system designer.

Depending upon the application, it may automatically prompt the user for a passcode as the application may not make privacy enabling optional. However, if privacy enablement is optional, the user would be offered the option at 58. If the user elects for privacy at 58, the system prompts for the passcode at 60. This user interface may appear such as that shown in FIG. 6.

One aspect of the embodiments may include a timer that monitors periods of inactivity. If the timer elapses during the period of inactivity, the device may prompt the user to re-enter the passcode prior to allowing the user access to the application. The timer starts at 62, just before, after or at the same time access is allowed to the server at 64.

Figure 4:
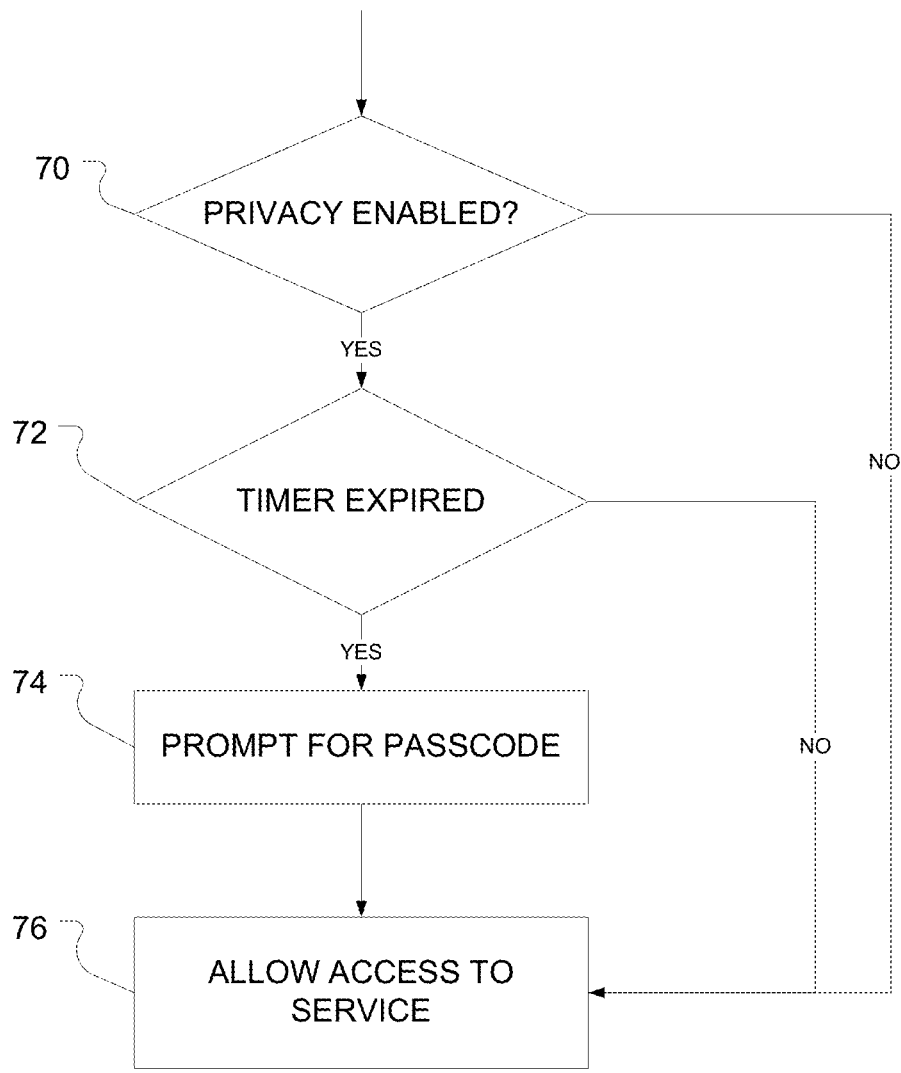
FIG. 4 shows an embodiment of providing a privacy-enabled application on a mobile device.

FIG. 4 shows a flowchart of an embodiment of a method of providing a privacy-enabled application on a mobile device. Returning to 54 in FIG. 3, the mobile device determines that it is not the user's first access of the application and the discussion moves to FIG. 4. The device prompts the user about privacy enablement at 70. If privacy is enabled for the device at 70, the device also determines whether the timer has expired at 72. If the timer has expired at 72, the device prompts for the passcode at 74. An example of the user interface for the passcode is shown in FIG. 7. If privacy is not enabled or if the timer has not expired, access is allowed to the service at 76.

In this manner, application-specific security provides an extra layer of security for mobile devices. Unlike website security relying on user names, passwords, site keys and security questions, this layer of security is application-specific and based on the mobile device, rather than the web site.

It will be appreciated that several of the above-disclosed and other features and functions, or alternatives thereof, may be desirably combined into many other different systems or applications. Also that various presently unforeseen or unanticipated alternatives, modifications, variations, or improvements therein may be subsequently made by those skilled in the art which are also intended to be encompassed by the following claims.

What is claimed is:

1. A system, comprising:
a server computing device executing software instruction code to provide a privacy-enabled service to users; and
a mobile computing device executing an application in the form of software instruction code to allow the mobile computing device to access the privacy-enabled service on the server, the software instruction code causing the mobile computing device to:
open a user interface on the mobile device upon reception of an input control to access an application;
determine whether or not the access is a first access of the application on the mobile device;
receive a user name and password through the user interface when the access is the first access of the application;
determine that the application is privacy-enabled;
notify the user that the application is privacy-enabled and prompting the user for a application passcode used for the privacy-enabled application;
receive the passcode from the user;
start a timer for the application upon receiving the passcode from the user; and
associating the passcode with the privacy-enabled application, wherein the association with the privacy-enabled application resides on the device.

2. The system of claim 1, wherein the mobile computing device comprises one of a smart phone or a tablet.

3. The system of claim 1, wherein the privacy-enabled service comprises a survey service.

4. A mobile device, comprising:
a display screen;
an input control; and
a processor, the processor executing instructions to cause the mobile device to:
receive an input control identifying an application to open, wherein the application is a privacy enabled application to allow access to a privacy-enabled service on a server;
open a user interface on the display screen for the application;
determine, upon reception of the input control, whether or not it is a first access of the application on mobile device;
receive a user name and password through the user interface upon the first access of the application;
detect that the application is privacy-enabled;
provide a prompt to the user to enter an application passcode used with the privacy-enabled application;
start a timer when the application passcode is received from the user; and
associate the application passcode with the application on the mobile device, upon the first access of the application.

5. The mobile device of claim 4, wherein the mobile device comprises one of either a tablet or a smart phone.

6. The mobile device of claim 4, wherein the input control comprises one of a touch screen, a control button, a keyboard and a roller.

7. A method of providing privacy-enabled applications, comprising:

receiving, at a processor on a mobile device, an input from a user identifying an application to open on the mobile device;
determining, at the processor for the mobile device, that the input identifying the application is an initial access of the application;
opening, using the processor, a link to a server identified by the application through a network;
using the processor to determine that the application on the mobile device is privacy enabled, and that the server provides a privacy-enabled service;
prompting, from the processor on the mobile device, the user to enter a username and password to access the server;
prompting, from the processor on the mobile device, the user for the application passcode located on the mobile device, the application passcode associated with the application to enable privacy for the application; and
receiving, at the processor on the mobile device, the application passcode from the user;
enabling a time upon receipt of the passcode: and
associating the application passcode with the application on the device, wherein the association resides on the device.

8. The method of claim 7, further comprising monitoring the timer with the processor on the mobile device.

9. The method of claim 8, further comprising:
determining that the user has not accessed the application within a time period determined by the timer; and
logging the user out of the server and disabling the application on the mobile device.

10. The method of claim 8, further comprising:
receiving, at the processor on the mobile device, an input from the user indicating access to the application is desired;
prompting, from the processor on the mobile device, the user for the application passcode; and upon receipt of the application passcode, enabling the application.

\* \* \* \* \*